United States Patent
Stromberg et al.

(10) Patent No.: US 6,972,009 B1
(45) Date of Patent: Dec. 6, 2005

(54) SYSTEM RELATED TO INTRAVENOUS ANAESTHESIA

(75) Inventors: Stefan Per Axel Stromberg, Sigtuna (SE); Jan Gustav Jakobsson, Djursholm (SE)

(73) Assignee: Aneo AB, (SE)

( * ) Notice: Subject to any disclaimer, the term of this patent is extended or adjusted under 35 U.S.C. 154(b) by 0 days.

(21) Appl. No.: 10/130,056

(22) PCT Filed: Nov. 13, 2000

(86) PCT No.: PCT/SE00/02222

§ 371 (c)(1),
(2), (4) Date: Dec. 9, 2002

(87) PCT Pub. No.: WO01/36026

PCT Pub. Date: May 25, 2001

(30) Foreign Application Priority Data

Nov. 15, 1999  (SE) .................................. 9904123

(51) Int. Cl.[7] .............................................. A61M 5/00
(52) U.S. Cl. .................. 604/246; 604/247; 600/431
(58) Field of Search ........................ 604/890.1, 48, 604/80–85, 93.01, 118–119, 121, 131, 151–152, 604/246–262

(56) References Cited

U.S. PATENT DOCUMENTS

| | | | |
|---|---|---|---|
| 3,650,093 A * | 3/1972 | Rosenberg ........................ 96/6 |
| 4,217,911 A * | 8/1980 | Layton ........................ 600/561 |
| 4,253,501 A * | 3/1981 | Ogle ............................ 141/27 |
| 4,838,856 A * | 6/1989 | Mulreany et al. .............. 604/65 |
| 5,098,377 A * | 3/1992 | Borsanyi et al. .............. 604/30 |
| 5,569,181 A * | 10/1996 | Heilman et al. .............. 604/30 |
| 5,569,208 A * | 10/1996 | Woelpper et al. ........... 604/183 |
| 5,843,037 A * | 12/1998 | Uber, III ..................... 604/151 |
| 5,885,216 A * | 3/1999 | Evans et al. ................ 600/431 |
| 5,916,201 A | 6/1999 | Wilson, Jr. et al. |
| 5,968,014 A | 10/1999 | Neftel et al. |
| 6,059,747 A * | 5/2000 | Bruggeman et al. ........ 604/500 |
| 6,623,455 B2 * | 9/2003 | Small et al. ................ 604/131 |

FOREIGN PATENT DOCUMENTS

WO  01/10861  7/1991

* cited by examiner

*Primary Examiner*—Nicholas D. Lucchesi
*Assistant Examiner*—Catherine S. Williams
(74) *Attorney, Agent, or Firm*—Banner & Witcoff, Ltd.

(57) ABSTRACT

The invention shows that conditions can be created in intravenous anaesthesia in which single-patient parts and accessories are separated from multi-patient parts and accessories by utilisation of a filter preventing contaminating particles from migrating from single-patient parts and accessories to multi-patient parts and accessories.

35 Claims, 2 Drawing Sheets

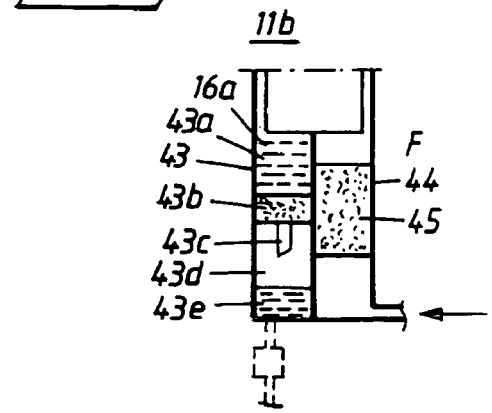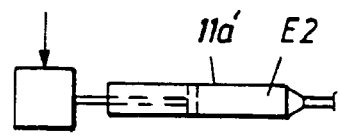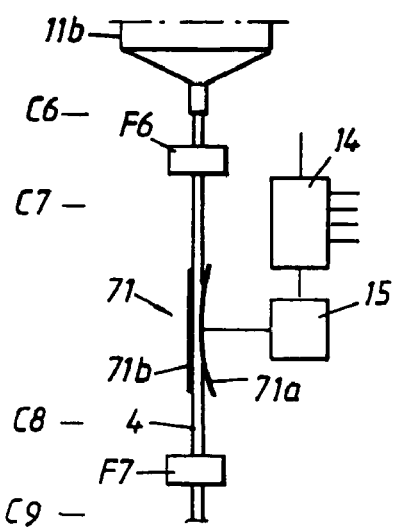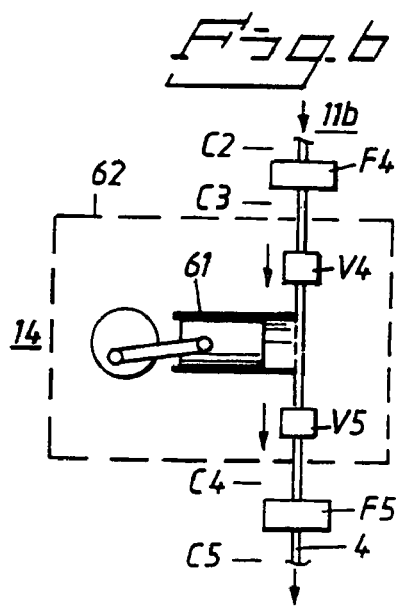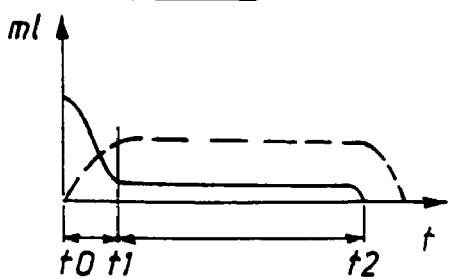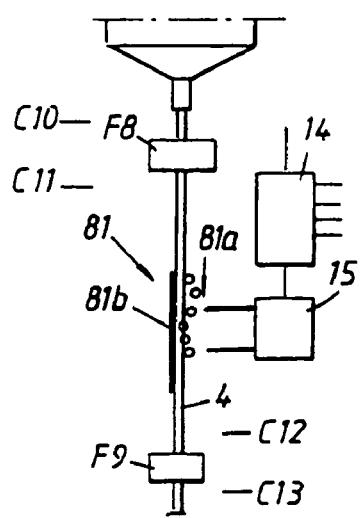

SYSTEM RELATED TO INTRAVENOUS ANAESTHESIA

This is a U.S. National Phase Application Under 35 USC 371 and applicant herewith claims the benefit of priority of PCT/SE00/02222 filed Nov. 13, 2000, which was published Under PCT Article 21(2) in English and Application No. 9904123-(8 filed in Sweden on Nov. 15, 1999.

FIELD OF THE INVENTION

The present invention relates to a system in intravenous anaesthesia and, more particularly, to a system for use in intravenous anaesthesia for adjustable delivery of fluid medication to a patient to be anaesthetised.

The present invention relates more particularly to a system comprising at least one container for the said fluid medication, a circuit for regulating the volume of medication supplied to the said patient per unit of time and a tube between the said container and the said patient.

The following description utilises the term "patient". "Patient" refers both to a person and to different animals requiring anaesthesia for surgical procedures.

PRIOR ART

Intravenous administration of a parenteral nutritional support solution, or a liquid comparable to a parenteral nutritional support solution, with a catheter, needle or cannula introduced into a vein, and connection of a tube between this cannula and a container holding the said parenteral solution, such as a saline solution or the like, positioned at a higher level than the patient, are previously known. In these applications, the container is normally hung on a stand.

A valve arrangement, through which the volume of fluid can be adjusted with different settings producing different tube choking, i.e. the volume of fluid administered per unit of time can be adjusted, is attached to the tube.

Arrangements of this kind are patient-related. This means that the container, tube, valve arrangement etc. which are relatively inexpensive, are discarded after the fluid has been administered, and no stringent demands are made on the accuracy of the rate of fluid administration. The pressure of fluid in the tube and cannula will depend on the height of the fluid container above the level of the patient.

No extreme demands are made on cleanliness, because the total amount of fluid in the container is selected and intended for only one patient and because the empty container with its associated valve arrangement and tube is discarded after infusion of the parenteral nutritional support solution or the like.

However, when intravenous anaesthesia is involved, greater demands must be made on accuracy in the rate of medication infusion, time-related variations in the rate set, the volume delivered and cleanliness.

In intravenous anaesthesia, the field to which the present invention relates, an anaesthesia-inducing drug is intravenously supplied to the patient, usually in large amounts during an initial phase in order to induce a desired depth of anaesthesia in the patient, followed by smaller amounts to keep the patient within suitable limits for the desired depth of anaesthesia.

Medication required for this purpose is supplied in containers holding standard volumes, concentrations etc. So estimating the time required for the suitable state of anaesthesia and the desired of anaesthesia and selecting a medication container volume, based on patient-related criteria (age, sex, race, weight etc.), corresponding to the time required to perform a surgical procedure, are also known.

However, such estimates have proved to be very rough, as every surgical procedure is unique and duration is difficult to determine in advance.

If an operation takes less time than estimated, too much medication could be left in the container and tube, i.e. a residual volume, which must be discarded. If an operation lasts longer than estimated, an empty medication container will have to be replaced with a new, full container.

This replacement of an empty container with a full one is an inconvenient circumstance during a surgical procedure, not the least because of the risk of erroneous connection, and the normal tendency is to start with a container whose volume of medication is excessive, thereby obviously increasing residual volume at the end of the surgical procedure.

If the selected volume still proves to be inadequate, the used, empty container must be replaced with a full container. Experience has shown that the excessive amounts of medication in the new container contributes to residual volume which must be discarded.

These containers are normally placed in an infusion unit in which the volume of medication infused per unit of time is regulated, making the replacement of an empty container with a full one a time-consuming step.

Analgesics and/or muscle relaxants are also commonly used in conjunction with the induction of anaesthesia with intravenous infusion of hypnotics and soporifics.

Containers, tubes etc. are also all devised for use with a single patient.

The risk of contamination is deemed to be too great for utilisation of one medication container with a plurality of patients, as bacteria, viruses and similar particles from a first patient could migrate up through the tube into medication in the container and be passed on to subsequent patients.

Medication contaminated in this way could then be supplied to a second, third, fourth patient etc. through use of the same cannula and/or the same container.

Different systems and devices for adjustable regulation of the administration of a fluid anaesthetic to a patient to be anaesthetised are previously known. An infusion unit pump, which by means of positive pressure in a container (a syringe arrangement), is used here to force medication through the tube and a cannula to a patient.

This application makes major demands on highly adjustable and accurately regulated administration of medication per unit of time and major demands on the control of this process, control being dependent upon detectable patient-related criteria.

The simplest embodiment of such a system for intravenous anaesthesia comprises at least one container for holding the said fluid medication, a circuit for regulating the volume of medication supplied to the patient per unit of time and a tube, between the said container or the said circuit and the said patient, one end of which being attached to a cannula inserted into a vein or the like.

The container, with tube and a valve arrangement, is normally conjoined into a single unit and can be located in an infusion unit containing a pump controlled by a control unit connected to the infusion unit.

This known arrangement is illustrated in greater detail in the following description of the embodiment shown in FIG. 2.

Utilisation of an infusion unit, with an associated control unit, in which the control unit is devised to controllably drive a stepper motor connected to a piston in a syringe on the basis of patient-related and other parameters in order to regulate and evaluate the amount of medication supplied per unit of time and the total amount of medication supplied, depending on the stepper motor's movements, is previously known.

The invention is therefore primarily devised for use in anaesthesia, more particularly in intravenous anaesthesia.

The present invention accordingly relates to and comprises a system permitting the infusion of a volume of fluid anaesthetic-inducing medication per unit of time into the blood of a living creature or a patient.

Here, the use of a lung ventilator and a monitoring and infusion unit, in which the latter, controlled by a control unit, is able to induce a depth of anaesthesia in the patient within limits selected for the depth of anaesthesia, is a practical necessity.

DESCRIPTION OF THE PRESENT INVENTION

Technical Problems

If the circumstance that the technical aspects someone well-versed in the art needs to consider in solving one or more technical problems is taken into account, insight is initially required into the steps and/or the sequence of steps which need to be taken and a choice of the requisite means. On the basis thereof, the following technical problems should be relevant in achieving the present invention.

With a view to the prior art as described above, creating conditions, using simple means, in which the volume of residual medication remaining after concluded surgery and conclusion of intravenous anaesthesia is kept to a minimum, largely irrespective of the duration of the state of anaesthesia, should be regarded as a technical problem.

Creating conditions, using simple means, enabling certain parts and accessories to be devised for single-patient use and for a small residual volume and other parts and accessories to be devised for multi-patient use without migration of contaminating particles from single-patient parts and accessories to multi-patient parts and accessories, is another technical problem.

Creating, using simple means, a distinct and readily distinguishable interface between parts and accessories for mufti-patient use and parts and accessories for single-patient use and preventing contaminating particles from migrating from the former to the latter should also be regarded as a technical problem.

Here, creating conditions, using simple means, enabling a depleted container for an anaesthesia-inducing drug to be refilled primarily with small amounts during the anaesthesia in an effort to keep residual volume low, especially at the end of anaesthesia, is a technical problem.

Being able to realise the importance of creating conditions in this technical field enabling a connection arrangement and/or some other and/or some additional connection arrangement, installed in the direction of flow, to be devised to prevent small contaminating particles from migrating into the said container during a normal flow of medication in one direction is a technical problem. The said connection arrangement is to be positioned so the residual volume is small.

Being able to realise the importance of subdividing a large-volume container into at least two parts, i.e. one part being a container (e.g. a syringe, pump or the like) holding a small volume of medication in the infusion unit and one part being a reserve container, directly or indirectly connected to the said container, holding a larger volume of medication, is a technical problem.

Being able to realise the importance and advantages of providing the infusion units container with a connector for medication refilling is also a technical problem. This connection must be located adjacent to or consist of a container outlet for medication.

Being able to realise the importance and advantages of devising an infusion unit control unit so it first empties the contents of the infusion unit container and then transfers small amounts of anaesthesia-inducing medication to the said container from a reserve container, thereby keeping residual volume small, is also a technical problem.

Being able to realise the importance of interposing a valve arrangement, comprising e.g. a one-way valve, between the container and the reserve container is a technical problem.

Being able to realise the importance and advantages of arranging a filter, using simple means, in or adjacent to the connection arrangement, to prevent contaminating particles from crossing the interface between multi-patient parts and accessories and single-patient parts and accessories is also a technical problem.

Creating conditions, using simple means, permitting continuous administration of medication to the patient, although not by means of a continuous flow of fluid or medication, is also a technical problem.

Being able to realise the importance and advantages of equipping the said filter with a means for shutting off the continuous flow of medication is an additional technical problem.

Being able to realise the importance and advantages of arranging a filter, devised to keep bacteria, viruses and similar contaminating particles from reaching medication in the reserve container, between a container and a reserve container, thereby making possible the use of medication in the reserve container as a supplementary volume for use with a plurality of different people or patients, is an additional technical problem.

Being able to realise the importance and advantages of arranging a shutoff valve between the reserve container and the connection arrangement is also a technical problem.

Within the scope of the invention, a selected container and/or reserve container can consist of a rigid container, or both the container and/or the reserve container can consist of a flexible container.

Providing the said connection arrangement with a common arrangement for transferring medication from and sending air to the reserve container, especially when the reserve container is a rigid container, is a technical problem.

Being able to realise the importance and advantages of having a dual-passage filter or connection arrangement, i.e. with one medication passage and one air passage separated from each other, a filter for impeding airborne bacteria, viruses and other contaminating particles being arranged in the air passage, is also a technical problem.

Being able to realise the importance and advantages of using an infusion unit container with a first volume corresponding to the volume required during an initial phase of anaesthesia in order to induce a desired depth of anaesthesia in the patient is an additional technical problem. After the initial phase, the infusion unit is devised to supply the patient, with a smaller volume of medication per unit of time in order to keep the patient within suitable limits for a desired of anaesthesia.

Being able to realise the importance of utilising a three-way connector, connected to the container, the reserve container and patient tube, with one-way valves in a line to the reserve container and tube, a one-way valve for the reserve container being devised to permit the passage of medication only at a pressure exceeding a pre-selected value somewhat greater than hydrostatic pressure from the reserve container is an additional technical problem.

Technical considerations are involved and technical problems must be resolved in realising that a filter must be arranged, upstream and/or downstream from a one-way filter, and/or that a one-way filter can be arranged upstream and/or downstream from the said filter.

Being able to realise the importance and advantages of conjoining a one-way valve and a filter and locating them close to each other is a technical problem. An interface can also be arranged between the three-way connector and the one-way valve. As an alternative, the said interface can be arranged upstream from the filter, preferably close to the reserve container.

Being able to realise the importance and advantages of using an infusion unit container, with a second volume less than a first volume, devised for initially inducing a desired depth of anaesthesia in the patient by means of a selected number of emptyings and refillings of the said second volume, the infusion unit being devised to deliver a smaller amount of medication per unit of time after the initial phase in order to keep the patient within suitable limits for the desired depth of anaesthesia, is a technical problem.

Being able to realise the importance and advantages of connecting the tube to the filter and having the interface downstream and/or downstream from the said filter is a technical problem.

Being able to realise the importance and advantages of having the regulatory circuit consist of e.g. a piston-cylinder arrangement with one-way valves on either side, the reciprocal motion of the piston being controlled by a control circuit in the infusion unit, thereby providing an opportunity for conjoining the said piston-cylinder arrangement and the said one-way valves in a single unit whose external shape is devised to fit the shape of a recess for an infusion unit container, a filter being provided upstream and/or downstream from the said unit, the said interface being provided downstream and/or upstream from the said filter, is a technical problem.

Being able to realise the importance and advantages of arranging the tube between a container with a large volume, through one or more filters and a medication-regulating circuit, and a cannula or the like, is a technical problem.

Being able to realise the importance and advantages of devising the said circuit choke off and/or open the tube cross-section, using a plate or similar peripheral part of the control unit, in order to regulate the supply of medication, the said filter being arranged downstream and/or upstream from the said circuit, is a technical problem.

Being able to realise the importance and advantages of devising the medication-regulating circuit to control the supply of medication solely on the basis of patient-related criteria, the supply of medication being arranged to be provided from a container above the level of the patient, is a technical problem.

Being able to realise the importance and advantages of devising the said circuit to choke off and/or open the tube cross-section by means of a pump or a similar peripheral part of the control unit in order to regulate the supply of medication is a technical problem. One or more filters can then be arranged downstream and/or upstream from the said pumping unit, an interface being arranged downstream and/or upstream from a filter.

Solution

The present invention is based on a system for adapting the administration of fluid medication, in intravenous anaesthesia, to a patient to be anaesthetised, the said system thereby comprising at least one container to hold the said fluid medication, a circuit for regulating the volume of medication delivered to the said patient per unit of time and a tube between the said circuit and/or container to the said patient, a connection arrangement being provided between the said container and the said tube and arranged to enable medication to flow from the said circuit and/or container through the said tube to the patient.

In order to solve one or more of the aforementioned technical problems, the present invention shows that the connection arrangement can consist of a filter devised to separate multi-patient parts and accessories from single-patient parts and accessories, and the said filter forms an interface preventing contaminating particles from migrating to the former parts and accessories.

As a further refinement of the invention concept, one connection arrangement and/or another and/or some additional connection arrangement arranged in the direction of flow is/are devised to prevent the passage of small contaminating particles to the said container during the normal flow of medication in one direction, and the connection arrangement is arranged to keep residual volume small.

With a system of the kind described above, the present invention also sets forth, as ideas for future lines of development, subdivision of the container into at least two parts, i.e. one part being a container in an infusion unit and one part being a reserve container connected to the said container.

In addition, the present invention shows that the infusion unit container has a medication filler connector located near an outlet or consists of a medication outlet.

In addition, the present invention shows that the infusion unit's control unit is devised and controllable so it first empties the contents of the infusion unit container and then sequentially transfers small amounts of medication from the reserve container, thereby keeping residual volume small.

The invention also shows that a valve arrangement, comprising at least one one-way valve, is arranged between the container and the reserve container.

In addition, the present invention shows that the said filter, devised to block the migration of bacteria, viruses and similar contaminating particles into medication held in the reserve container, is arranged between the container and the reserve container.

A valve can also be arranged between the reserve container and the connection arrangement.

The reserve container and/or the container can consist of a rigid container (flask) or, more advantageously, a flexible container (bag). With a rigid container, the said connection arrangement must have an arrangement for sending air to the reserve container.

This shows that the connection arrangement must have two parts, i.e. one passage for medication and one passage for air, a filter being arranged in the air passage to block the passage of airborne bacteria, viruses and similar contaminating particles.

The invention sets forth that the infusion unit container shall have a first volume corresponding to the amount of medication required in order to induce a desired depth of anaesthesia during an initial phase.

The infusion unit is devised to supply the patient with smaller amounts of medication per unit of time, after the initial phase, in order keep the patient within appropriate limits for the desired depth of anaesthesia and achieve small residual volumes.

A three-way connector is connected to the container, reserve container and patient tube with one-way valves arranged in a line to the reserve container and tube.

The reserve container's one-way valve is devised to permit the passage of medication only at a pressure exceeding a pre-selected value, i.e. somewhat higher than hydrostatic pressure from the reserve container.

A filter can advantageously be arranged upstream from the said one-way valve, and a one-way valve can advantageously be arranged upstream from the said filter.

A shut-off and/or opening valve can be arranged upstream from the said one-way valve.

A one-way valve and a filter can be interconnected near each other.

Here, the said interface can be arranged between the three-way connector and the one-way valve.

The said interface can therefore be arranged upstream from the filter, and/or the interface can be arranged next to the reserve container.

A container for an infusion unit can have a second volume, smaller than the said first volume, devised for initially inducing a desired depth of anaesthesia with a selected number of emptyings and refillings of the said second volume during an initial phase.

The infusion unit is devised to deliver, after the initial phase, a smaller amount of medication per unit of time to the patient in order to keep the patient within appropriate limits for the desired depth of anaesthesia.

Here, the tube can be connected to the filter, and the interface can be arranged downstream and/or upstream from the said filter.

The regulatory circuit can consist of a piston-cylinder arrangement or the like with a one-way valve on either side, the piston's reciprocal movement being controlled by a control circuit in an infusion unit.

The said piston-cylinder arrangement and the said one-way valves are conjoined into a physical unit whose external shape can be made to fit exactly into an infusion unit recess intended and devised for a container.

The invention also shows that a filter is arranged upstream from the said unit, and the said interface is arranged downstream and/or upstream from the said filter.

A tube can be arranged between a container with a large volume, through one or more filters, past a medication-regulating circuit and a cannula or the like.

Here, the said circuit is devised to choke off and/or open a section of tube, by the action of a control unit plate or the like on the periphery of the tube, in order to regulate the supply of medication.

The said filter is arranged downstream and/or upstream from the said circuit, and the said interface can be arranged downstream and/or upstream from the said filter.

The medication-regulating circuit is devised to control the delivery of medication solely on the basis of patient-related criteria, the delivery of medication being advantageously arranged for provision from a container above the level of the patient.

The said circuit is also devised to choke off and/or open a section of tube, by the action of a pump or a control unit on the periphery of the tube, in order to regulate the supply of medication.

Here, the invention proposes that one or more filters be arranged downstream and/or upstream from the said pumping unit.

The said interface can then be arranged downstream and/or upstream from one or more filters.

The medication-regulating circuit can also be arranged to control the delivery of medication on the basis of patient-related criteria, the volume of medication supplied etc., although only taking into account information on the volume of medication supplied per unit of time or the total volume supplied.

Even here, the delivery of medication can be devised to take place from a container above the level of the patient.

Advantages

The main advantages of a system according to the invention are that the system creates, using simple means, conditions for devising certain parts and accessories for multi-patient use while other parts are devised for single-patient use through the use of a connection arrangement, preferably in the form of a filter between them, single-patient parts and accessories being devised for small residual volumes, thereby limiting undesirable amounts of residual anaesthesia-inducing medication which would have to be thrown out.

This is achieved in practice by use of an infusion unit container whose volume of medication is devised to be equal to or somewhat less than the volume likely to be needed for a suitable duration of anaesthesia, a desired depth of anaesthesia and other relevant criteria. If more medication should be needed, small amounts can be successively supplied from a reserve container, thereby creating conditions for keeping residual volume small at the end of anaesthesia.

This accordingly reduces the volume of medication which is normally removed and thrown out because the infusion unit's volume of medication is greatly over-dimensioned for safety reasons. A connection arrangement and filter simultaneously prevent contaminated medication from a patient from migrating into medication intended for one or more other patients.

The main significant feature in a system for regulating the supply of fluid medication to a patient in whom narcosis is to be induced by means of intravenous anaesthesia is set forth in the characterising part of patent claim 1.

BRIEF DESCRIPTION OF THE FIGURES

Two previously known systems for intravenous administration of fluids and medication to a patient, as well as a system set forth in the invention, will now be described in greater detail, referring to the attached drawings in which:

FIG. 4 shows a longitudinal section of a proposed connection arrangement with a filter for a medication passage and an air passage;

FIG. 5 illustrates the principles of a second embodiment according to the invention;

FIG. 6 illustrates the principles of a third embodiment according to the invention;

FIG. 7 illustrates the principles of a fourth embodiment according to the invention;

FIG. 8 illustrates the principles of a fifth embodiment according to the invention;

FIG. 9 is a time diagram illustrating variations in the amount of medication administered during anaesthesia.

DESCRIPTION OF PRIOR ART

Figure 1:
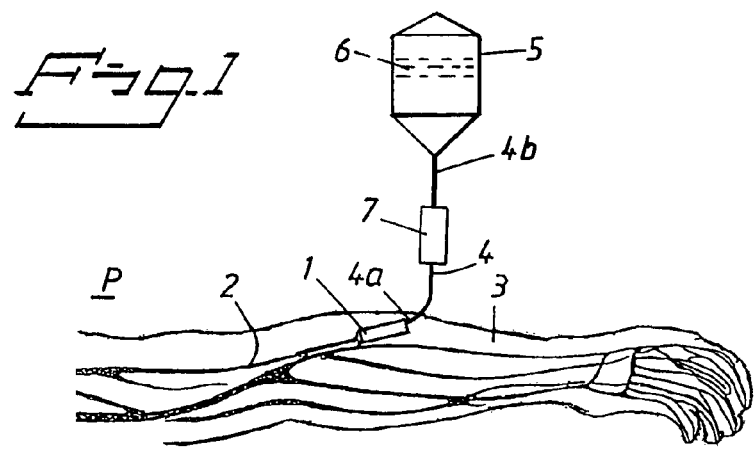
FIG. 1 illustrates the principle for intravenous administration of a parenteral nutritional support solution to a patient from a container in which the fluid can consist of e.g. a saline solution.

FIG. 1 is a drawing of a system for adjustable, limited-precision regulation of a parenteral nutritional support liquid, such as a saline solution, for intravenous administration to a person.

FIG. 1 shows a cannula 1 inserted into a vein 2 in an arm 3.

The cannula 1 is connected to a tube 4, one end 4a of which is connected to the said cannula 1 and the other end 4b is connected to a container 5, usually a flexible plastic container holding a fluid 6, e.g. a saline solution.

Here, a valve arrangement 7 is attached to or arranged around the tube 4, and the volume of fluid administered per unit of time can be regulated by the action of the valve arrangement 7 in the known manner.

It should be noted that no great accuracy is needed in the administration of fluid for this application. So a simple valve arrangement 7 can therefore be used when the amount of fluid administered per unit of time is not critical.

In addition, large flows, e.g. up to 500 ml/hour or even more in some instances, can be delivered with this valve arrangement.

A system for regulating the amount of fluid medication administered to a patient to be anaesthetised requires far greater precision.

The process entails initially administering a large flow and then greatly reducing the flow to an adjustable level, thereby achieving a desired depth of anaesthesia. This is illustrated in FIG. 9.

Figure 2:
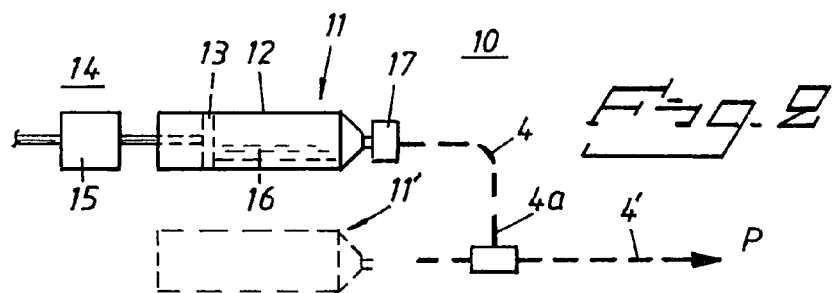
FIG. 2 shows the principle parts of an infusion system for adjustable administration of medication to a person in intravenous anaesthesia.

FIG. 2 is a schematic rendition of a syringe 11 with a container 12, a piston 13 and a control unit 14, containing a stepper motor 15, in an infusion unit 10.

The system according to FIG. 2 comprises at least one container 12 for fluid medication 16 and a regulatory circuit or control unit 14 for regulating administration of a volume of medication per unit of time to the said person.

In addition, a tube 4 is arranged between the said container 12 and the said patient P.

A connection arrangement 17 between the said container 12 and the said tube 4 is arranged to enable medication 16 to flow from the said container 12, via the said control unit 14 and the said tube 4, to the patient P.

FIG. 2 shows that one tube end 4a is connected to a three-way connector or the equivalent to enable one or more containers 11, 11' to be connected to the tube 4', one end of which is arranged for connection to the cannula 1.

DESCRIPTION OF PROPOSED EMBODIMENTS

The invention is based on the experience that users commonly select a much larger volume of medication 16 than the volume consumed during anaesthesia to avoid the need to replace an empty syringe 11 with a new one or refill an empty syringe with medication during surgery.

So large residual volumes remain and cannot be saved for use with another patient due to the risk of infection.

The invention is based on a system for regulated adaptation of the fluid medication administered to a patient to be anaesthetised during intravenous anaesthesia, the said system comprising at least one container to hold the said fluid medication, a regulatory circuit or control unit for regulating the volume of medication administered per unit of time and a tube between the said circuit or container and the said patient, a connection arrangement being provided to permit the passage of medication from the said container to the patient.

A filter, linked to the connection arrangement, is devised to separate multi-patient parts and accessories from single-patient parts and accessories. The said filter forms an interface preventing contaminating particles from migrating to the former parts and accessories.

This means that the volume of medication 16 can be somewhat less, by a wide margin, than the volume calculated as necessary for inducing anaesthesia, and a supplementary volume of medication can be sent to the syringe 11 from a reserve container 11a.

The container 1a and the reserve container 11b interact by means of a connection arrangement 31 which could contain valves (V1, V2) and a filter (F1).

The said connection arrangement 31 and/or some other and/or some additional connection arrangement with filters, arranged in the direction of flow, is devised to prevent the migration of small contaminating particles to the said container 11b and/or container 11a during a normal flow of medication through the tube 4 in a given direction. The connection arrangement is arranged to ensure that residual volume is small.

Figure 3:
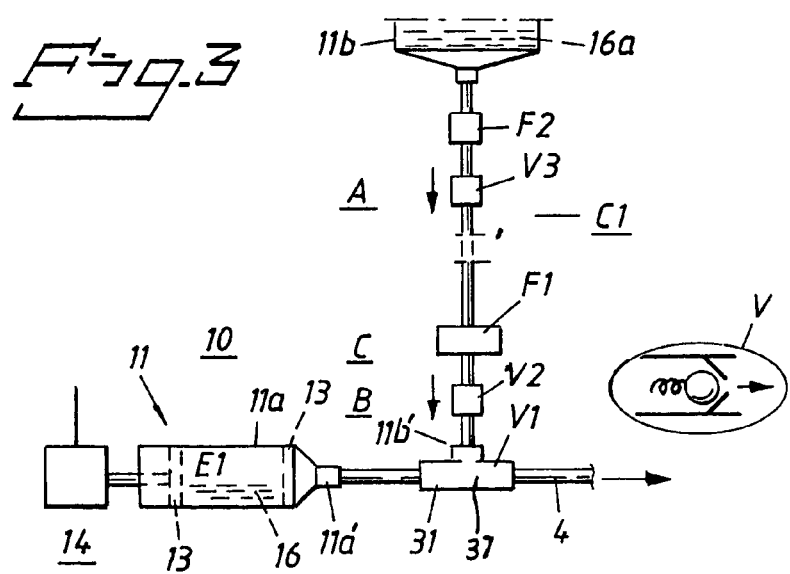
FIG. 3 illustrates the principles of a first embodiment according to the invention.

FIG. 3 shows that the container 11 is divided into at least two parts 11a, 11b, one being a container or syringe 11a, holding a selected small volume of medication, in an infusion unit 10 and one being a reserve container 11b, holding a large volume of medication, connected to the said container 11a.

Here, the volume of medication for the container 11a can be selected for reasons other than the estimated duration of the surgical procedure and be much smaller, as a sufficient reserve volume is available in the reserve container 11b.

The invention sets forth the use of one or more filters F, and this/these filter(s) separate(s) multi-patient parts and accessories A from single-patient parts and accessories B.

The filter F forms an interface C preventing contaminating particles from migrating from single-patient parts B to multi-patient parts A.

Single patient parts and accessories B are devised to have a small residual volume at the end of anaesthesia. This means that e.g. the container 11a should then be virtually empty. Other parts and accessories are selected for a small residual volume.

FIG. 3 is a schematic depiction of a first embodiment with the features associated with the present invention.

The infusion unit's 10 container 11a has a connector 11b' through which medication can be filled, and the connector is arranged close to or consists of a medication outlet 11a'.

An infusion unit's 10 control unit 14 can be devised to empty the contents of the infusion unit's container 11a and then transfer small amounts of anaesthesia-inducing medication, as needed and successively, from the reserve container 11b to keep residual volume small in single-patient parts.

This can be achieved when a piston 13 performs reciprocal movements within the dashed range shown in FIG. 3 in order to pump medication from the container 11b to the container 11a and from the container 11a, via a three-way connector 37 of the connection arrangement 31 and the tube 4, to the patient.

The anaesthesia can now be concluded with a small residual volume because the container 11a is empty, and tubing has a small cross-section.

A number of valve arrangements V, each of which containing a one-way valve, is arranged between the container 11a and the reserve container 11b.

A first one-way valve V1 is built into or connected close to the three-way connector 37, and a second one-way valve V2 is built into or close to the three-way connector 37 path to the reserve container 11b.

The one-way valve V2 is connected to a first filter F1.

As an alternative, a filter F2 and a one-way valve V3 can be connected close to the reserve container 11b.

The filter F1 and one-way valve V2 can be omitted in certain applications. The selected interface is then moved to the position designated C1.

The filter F1 and/or the filter F2 are designed to block the access of bacteria, viruses and similar contaminating particles to medication 16a in the reserve container 11b.

The reserve container 11b and/or the container 11a can advantageously be flexible or rigid containers.

When a rigid container 11b is utilised, an arrangement is proposed for feeding air into the reserve container 11b as it empties of medication 16a.

There is nothing to prevent having an outlet for medication and an inlet for air.

FIG. 4 shows that a combined arrangement of this kind can be divided into two parts, i.e. with a passage 43 for medication and a passage 44 for air, and a filter 45 is arranged in the air passage to prevent bacteria, viruses and similar contaminating particles from passing from ambient air into the container 11b.

The medication passage 43 has an upper space 43a filled with medication 16a. This medication passes through a filtering unit 43b and, via a drip nozzle 43c in which drops traverse a gas-filled (air-filled) space 43d to a space 43e before passing through some additional filter F3 or a valve.

FIG. 3 also shows the use of an infusion unit's 10 container 11a with a first large volume 11a intended for rapidly inducing a desired depth of anaesthesia in an initial phase.

The infusion unit is also devised to deliver smaller amounts of medication per unit of time, after the initial stage, in order keep the patient within appropriate limits for the desired depth of anaesthesia.

Here, it should be noted that the amount of hypnotic proposed for administration during the initial phase t0 to t1 can be 10 to 30 ml administered over 3 to 4 minutes, e.g. 20 ml over 2 minutes. The amount supplied during the remaining time t1 to t2 can be 50 to 100 ml/hour. The total volume administered during the anaesthesia can be 100 to 500 ml.

Here, it should be noted that the amount of analgesic proposed for administration during the initial phase t0 to t1 can be 1 to 2 ml. The amount administered during the remaining time can be 10 to 50 ml/hour.

Here, it should be noted that the amount of muscle relaxant proposed for administration during the initial phase t0 to t1 can be 3 to 5 ml. The amount administered during the remaining time can be 3 to 5 ml/hour.

It should be noted that each of the aforesaid agents requires a separate infusion unit and control unit.

Hypnotics can be advantageously administered sequentially. Long-acting analgesics can also be advantageously administered sequentially, whereas muscle relaxants can be administered continuously under controlled conditions.

A three-way connector 37 is connected to the container 11a, the reserve container 11b and the patient tube 4 by one-way valves in the line to the reserve container 11b and the tube 4. One or more filters can be built into the three-way connector 37.

The one-way valve (V2) for the reserve container 11b is devised to allow the passage of medication 16a only at a pressure, exceeding a pre-selected value, somewhat higher than hydrostatic pressure from the reserve container 11b.

A filter F1 is arranged upstream somewhat from the said one-way valve V2, and an additional one-way valve V3 is arranged upstream from the said filter F1.

A shut-off and/or opening valve (not shown) can be arranged upstream from the said one-way valve V3.

A one-way valve V2 (V3) and a filter F1 (F2) can advantageously be interconnected close to one another and form a single unit.

The interface C can advantageously be arranged between the three-way connector 31 and the one-way valve V2, but there is nothing to prevent arrangement of the interface upstream from the filter F1 and/or close to the reserve container 11b.

FIG. 5 shows an alternative to FIG. 3 in which the infusion unit's 10 container 11a' has a second volume E2, much smaller than the first volume E1, the former being devised to deliver a desired depth of anaesthesia in the patient with a selected number of emptyings and fillings of the said second volume E2 during an initial phase.

It is proposed that the volume E2 be selected so 2–5 emptyings are needed for the delivery of a sufficient volume of medication during the initial phase.

The infusion unit is also devised to supply the patient, after the initial phase, with a smaller amount of medication per unit of time in order to keep the patient within appropriate limits for the desired depth of anaesthesia.

FIG. 6 shows an alternative embodiment in which the container 11a has been removed and medication is only supplied from one large container 11b.

Here, the tube 4 is connected to a filter F4 and/or F5, and one or more interfaces C2, C3, C4, C5 can be arranged downstream and/or upstream from the said filter.

Here, the regulatory circuit or control unit 14 consists of a piston-cylinder arrangement 61 with one-way valves V4, V5 on each side, the reciprocal movements of the piston being controlled by a control circuit 14 in the infusion unit.

The said piston-cylinder arrangement 61 and the said one-way valves V4, V5 are conjoined into a single unit 62 whose external shape fits the shape of an infusion unit recess devised to hold a container 11a.

Having the filter F4 arranged upstream from the said unit 62 may be important.

The said interface C2, C3 is arranged downstream and/or upstream from the said filter F4.

The embodiment according to FIG. 7 shows that a single tube 4 is arranged between a large-volume container 11b, through one or more filters F6 and F7 respectively, a medication-regulating circuit 71 and a cannula or the like.

The said circuit 71 is devised to choke off and/or open the tube cross-section, by means of a plate 71a or the like, a stop 71b and a control unit's 14 stepper motor 15, in order to regulate the delivery of medication.

The said filters F6, F7 are arranged downstream and/or upstream from the said circuit, and one or more interfaces C6, C7, C8, C9 are arranged downstream and/or upstream from the said filters F6, F7.

The medication-regulating circuit or control circuit 14 is devised to control the delivery of medication solely on the basis of patient-related criteria. The amount of medication delivered and/or volume per unit of time can be estimated in order to provide the surgeon with useful information but is not part of the control process. These amounts can be obtained from the control unit and the setting set for the stepper motor.

Patient-related criteria and the choice of same can be made in the manner shown and described in Swedish patent application no. 9901688-(3, filed on 10 May 1999 and entitled "Arrangemang för att kunna tilidela en levande varelse ett anestesialt tillstånd" (i.e. Arrangement for inducing a state of anaesthesia in a living creature).

The contents of the said patent application shall be regarded as a part of this application.

Here, the administration of medication shall be devised to take place from a container 11b above the level of the patient.

FIG. 8 shows that the control unit 14 causes a medication-regulating circuit 14 with a stepper motor 15 to choke off and/or open the cross-section of a tube 4 by means of a pump (with a peristaltic action to force fluid or medication downstream) or similar unit 81 on the periphery of the tube in order to thereby regulate the delivery of medication. A moving means 81a, acting against a fixed plate 81b, is arranged here.

Filters F8, F9 are arranged downstream and/or upstream from the said pumping unit 81, and the said interfaces, such as C10, C11, C12, C13, can be arranged downstream and/or upstream from the filter F8 and F9 respectively.

The medication-regulating circuit is primarily arranged for regulating the delivery of medication according to patient-related criteria and from information on the momentary amount of medication supplied per unit of time.

FIG. 9 shows, using a solid line, that a relatively large volume of medication is supplied during an initial phase t0 to t1 in order to quickly induce a state of anaesthesia in the patient. The desired depth of anaesthesia is illustrated with a dashed line.

A relatively small, regulated amount of anaesthesia-inducing medication is given to the patient for a brief period of time t1–t2 in order to keep the patient at the desired depth of anaesthesia or for controlled regulation of the depth of anaesthesia.

The possibility of supplying medication in an amount and at a rate consistent with empirical values while using values for patient criteria for regulating the period from t1 to t2 also falls within the scope of the invention.

The "successive" administration of medication or agents means that an empty container (11a) is refilled with a given amount (1/2). This amount is emptied and then refilled to a lesser degree (114) etc.

The invention is clearly not limited to the exemplary embodiments above but can be modified within the scope of the invention concept as illustrated in the following patent claims.

What is claimed:

1. A system for controllably regulating the administration of fluid medication to a patient to be anaesthetised with intravenous anaesthesia, said system comprising an infusion container for holding and introducing the fluid medication to a single patient, said infusion container including a connector positioned proximate an outlet of said infusion container through which said infusion container can be filled with, and emptied of, the fluid medication, a reserve container for containing a portion of the fluid medication that can be transferred to said infusion container, said reserve container being useable with multiple patients, a control unit including a circuit for regulating the volume of medication delivered from the infusion container to said patient per unit of time, said control unit operates to empty the fluid medication from said infusion container and transfer small amounts of fluid medication from said reserve container to said infusion container, a tube between said circuit or said infusion container and said patient, a connection arrangement provided to allow the passage of the fluid medication from said infusion container to the patient and from said reserve container to said infusion container, said connection arrangement comprising a first filter, a first one-way valve positioned between said tube and said first filter and a second valve, and a second filter positioned upstream of said connection arrangement between said connection arrangement and said reserve container, at least said first filter and first valve being positioned to separate multi-patient parts including said reserve container from single-patient parts including said infusion container and form an interface preventing contaminating particles from migrating into at least the reserve container.

2. The system according to claim 1, wherein the reserve container is connected or adjacent to said infusion container.

3. The system according to claim 1, wherein the reserve container is a rigid container.

4. The system according to claim 1, wherein the reserve container is a flexible container.

5. The system according to claim 3, wherein said connection arrangement has an arrangement for sending air to the reserve container.

6. The system according to claim 3, wherein the reserve container is divided into two parts including a medication passage and an air passage, and wherein a filter devised to block airborne bacteria, viruses and similar contaminating particles is arranged in the air passage.

7. The system according to claim 1, wherein infusion container has a first volume selected to correspond to the volume of medication needed during an initial phase for inducing a desired depth of anaesthesia in the patient.

8. The system according to claim 7, wherein the infusion unit is devised to deliver, after the initial phase, smaller amounts of medication per unit time from the infusion container in order to keep the patient within suitable limits for the depth of anaesthesia.

9. The system according to claim 7, wherein said connection arrangement comprises a three-way connector that is connected to the infusion container, reserve container and patient tube.

10. The system according to claim 9, wherein said one-way valve is devised to permit the passage of medication only at a pressure exceeding a pre-selected value that is greater than hydrostatic pressure from the reserve container.

11. The system according to claim 1, wherein said first filter is arranged upstream from said one-way valve.

12. The system according to claim 1, wherein said one-way valve is arranged upstream from said filter.

13. The system according to claim 12, wherein said second valve is a shut-off and/or opening valve located upstream from said one-way valve.

14. The system according to claim 1, wherein said one-way valve and first filter are conjoined or located near each other.

15. The system according to claim 1, wherein said connector includes a three-way connector, and said interface is arranged between the three-way connector and the one-way valve.

16. The system according to claim 1, wherein said interface is arranged upstream from said second filter.

17. The system according to claim 1, wherein said interface is arranged next to the reserve container.

18. The system according to claim 1, wherein said infusion container has a second volume, smaller than a first volume, for initially inducing a desired depth of anaesthesia in a patient, by employing a selected number of emptyings and fillings of said second volume during an initial phase in order to induce a desired depth of anaesthesia in a patient.

19. The system according to claim 18, wherein the infusion unit is devised to deliver, after the initial phase, a smaller amount of medication per unit of time in order to keep the patient within suitable limits for the desired depth of anaesthesia.

20. The system according to claim 1, wherein the tube is connected to one of said filters, and the interface is arranged downstream or upstream from said one of said filters.

21. The system according to claim 1, wherein the control unit comprises a piston-cylinder arrangement with a one-way valve on each side thereof, and the reciprocal movements of said piston are controlled by a control circuit.

22. The system according to claim 21, wherein said piston-cylinder arrangement and said one-way valves on either side of said piston-cylinder arrangement are conjoined in a single unit whose external shape fits the shape of an infusion unit recess devised for said infusion container.

23. The system according to claim 21, wherein at least one filter is arranged upstream or downstream from said single unit.

24. The system according to claim 23, wherein said interface is arranged downstream or upstream from one of said filters.

25. The system according to claim 1, wherein the tube is arranged between said reserve container, through at least one of said filters and said medication regulating circuit, and a member for inserting within the patient.

26. The system according to claim 25, wherein said control unit includes a choking member, and said circuit is devised to have the control unit choke off and/or open a section of tube, in order to regulate the administration of medication.

27. The system according to claim 25, wherein at least one of said filters is arranged downstream or upstream from said circuit.

28. The system according to claim 1, wherein said interface is arranged downstream or upstream from said second filter.

29. The system according to claim 25, wherein the medication-regulating circuit is devised to control the administration of medication solely on the basis of patient-related criteria.

30. The system according to claim 26, wherein the infusion unit is positioned above the patient during use such that the administration of medication is arranged to take place from the infusion container located above the level of the patient.

31. The system according to claim 25, wherein said control unit includes a choking member, and said circuit is devised to have the choking member of said control unit choke off and/or open a section of tube in order to regulate the administration of medication.

32. The system according to claim 31, wherein at least one of said filters is arranged downstream or upstream from said choking member.

33. The system according to claim 31, wherein an interface is arranged downstream or upstream from said second filter.

34. The system according to claim 31, wherein the medication regulating circuit is arranged to control the administration of medication on the basis of patient-related criteria including on the basis of information on the volume of medication supplied per unit of time.

35. The system according to claim 31, wherein the infusion unit is positioned above the patient during use such that the administration of medication is arranged to take place from the infusion container located above the level of the patient.

* * * * *